US011607145B2

(12) United States Patent
Zhu et al.

(10) Patent No.: US 11,607,145 B2
(45) Date of Patent: Mar. 21, 2023

(54) TECHNIQUES FOR DETERMINING CHARACTERISTICS OF DIALYSIS ACCESS SITES USING IMAGE INFORMATION

(71) Applicant: Fresenius Medical Care Holdings, Inc., Waltham, MA (US)

(72) Inventors: Fansan Zhu, Flushing, NY (US); Peter Kotanko, New York, NY (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 497 days.

(21) Appl. No.: 16/678,247

(22) Filed: Nov. 8, 2019

(65) Prior Publication Data

US 2021/0137394 A1 May 13, 2021

(51) Int. Cl.
*A61B 5/00* (2006.01)
*A61B 5/026* (2006.01)
(Continued)

(52) U.S. Cl.
CPC .......... *A61B 5/0261* (2013.01); *A61B 5/0077* (2013.01); *A61B 5/1032* (2013.01);
(Continued)

(58) Field of Classification Search
CPC ... A61B 5/0261; A61B 5/0077; A61B 5/1032; A61B 5/1128; G06F 16/2474; G16H 20/40
See application file for complete search history.

(56) References Cited

U.S. PATENT DOCUMENTS 6,692,443 B2 2/2004 Crutchfield et al.
2009/0080757 A1* 3/2009 Roger ................. A61M 1/3653
382/134

(Continued)

OTHER PUBLICATIONS

Phinyomark et al., A Novel Feature Extraction for Robust EMG Pattern Recognition, Journal of Computing, vol. 1, Issue 1 (Dec. 2009); available at https://arxiv.org/ftp/arxiv/papers/0912/0912.3973.pdf (Year: 2009).*

(Continued)

*Primary Examiner* — Christopher L Cook
*Assistant Examiner* — Mehdi Poursoltani
(74) *Attorney, Agent, or Firm* — Seager, Tufte & Wickhem, LLP

(57) ABSTRACT

A dialysis access site monitoring system may generate a treatment recommendation for treating a condition of an access site based on a video of the access site. The dialysis access site monitoring system may include an apparatus having a processor and a memory coupled to the processor. The memory may include instructions that, when executed by the processor, may cause the processor to generate video information based on a video of a dialysis access site of a patient, determine change in the number of pixels (CNP) information of the video information, the CNP information associated with movement of a skin surface of the patient due to blood flow through the dialysis access site, determine frequency domain information of the CNP information, determine a maximum-to-median power (M2) value of the frequency domain information, and determine at least one access site characteristic based on the M2 value.

16 Claims, 12 Drawing Sheets

(51) Int. Cl.
    *G06F 16/2458*     (2019.01)
    *A61B 5/103*     (2006.01)
    *A61B 5/11*     (2006.01)
    *G16H 20/40*     (2018.01)

(52) U.S. Cl.
    CPC ........ *A61B 5/1128* (2013.01); *G06F 16/2474* (2019.01); *G16H 20/40* (2018.01)

(56) References Cited

U.S. PATENT DOCUMENTS

| | | |
|---|---|---|
| 2013/0274610 A1 | 10/2013 | Kamshilin et al. |
| 2014/0072190 A1 | 3/2014 | Wu et al. |
| 2014/0340502 A1 | 11/2014 | Freeman et al. |
| 2017/0119258 A1* | 5/2017 | Kotanko ............. A61M 1/3656 |

OTHER PUBLICATIONS

F. Zhu et al., "Estimation of arterio-venous access blood flow in hemodialysis patients using video image processing technique," 2016 38th Annual International Conference of the IEEE Engineering in Medicine and Biology Society (EMBC), 2016, pp. 207-210, doi: 10.1109/EMBC.2016.7590676. (Year: 2016).*

F. Zhu, F. Kappel, E. F. Leonard, P. Kotanko and N. W. Levin, "Modeling of change in blood volume and extracellular fluid volume during hemodialysis," 2013 35th Annual International Conference of the IEEE Engineering in Medicine and Biology Society (EMBC), 2013, pp. 1506-1509 (Year: 2013).*

F. Zhu, P. Kotanko and N. W. Levin, "Estimation of peripheral blood volume and interstitial volume in hemodialysis patients using bioimpedance techniques," 2017 39th Annual International Conference of the IEEE Engineering in Medicine and Biology Society (EMBC), 2017, pp. 1389-1392 (Year: 2017).*

Payette et al., Assessment of Skin Flaps Using Optically Based Methods for Measuring Blood Flow and Oxygenation, Plastic and Reconstructive Surgery: Feb. 2005—vol. 115—Issue 2—p. 539-546 (Year: 2005).*

Merletti et al., On-Line Monitoring of the Median Frequency of the Surface EMG Power Spectrum, IEEE Transactions on Biomedical Engineering, vol. BME-32, No. 1, Jan. 1985 (Year: 1985).*

International Search Report and Written Opinion for International application No. PCT/US2020/055960, dated Jul. 9, 2021, 11 pages.

Zhu, F., et al., "Assessment of fistula flow using smartphone video analysis", Journal of the American Society of Nephrology 30:39 (2019) Abstract.

Zhu, F., et al., "Assessment of Fistula Flow using Smartphone Video Analysis Session Information Category: Dialysis Authors Background" Washington DC-40 Conference [online] 2019 [retrieved on Oct. 4, 2021]. Retrieved from Internet URL: https://www.asn-online.org/education/kidneyweek/2019/program-abstract.aspxcontrolId=3232302, Abstract.

Wu, et al., "Eulerian Video Magnification for Revealing Subtle Changes in the World", ACM Trans Graph 31(4):1-8 (2012).

Nakajima, et al., "Detection of Apparent Skin Motion Using Optical Flow Analysis: Blood Pulsation Signal Obtained from Optical Flow Sequence", Rev Sci Instrum 68:1331-1336 (1997). Abstract.

Zhu, et al., "Estimation of Arterio-Venous Access Blood Flow in Hemodialysis Patients Using Video Image Processing Technique" 38th Annual Conf Proc IEEE Eng Med Biol Soc pp. 207-210 (2016). Abstract.

International Search Report and Written Opinion for International application No. PCT/US16/59885, dated Mar. 10, 2017, 9 pages.

Fishbane, S., et al., "Changes to the End-Stage Renal Disease Quality Incentive Program" Kidney International 81:1167-1171 (2012).

Salman, L., and Beathard, G., "Interventional Nephrology: Physical Examination as a Tool for Suveillance for the Hemodialysis Arteriovenous Access," Clin J Am Soc Nephrol, 8:1220-1227 (2013).

Haussecker, H., and Fleet, D.J., "Estimating optical flow with physical models of brightness variation" IEEE Transactions on Pattern Analysis and Machine Intelligence, 23:661-673 (2001). Abstract.

Campos, R.P., et al., "Accuracy of physical examination and intra-access pressure in the detection of stenosis in hemodialysis arterivenous fistula", Semin Dial 21(3):269-273 (2008).

Zhu, F., et al., "Assessment of Fistula Flow Using Smartphone Video Analysis" ASN abstract 2019 (submission).

\* cited by examiner

TECHNIQUES FOR DETERMINING CHARACTERISTICS OF DIALYSIS ACCESS SITES USING IMAGE INFORMATION

FIELD

The disclosure generally relates to processes for examining physical characteristics of a portion of patient based on one or more images of the portion, and, more particularly, to techniques for using video information to assess a characteristic of a dialysis access site of a patient.

BACKGROUND

Dialysis treatment requires access to the patient circulatory system via a dialysis access site in order to process patient blood using a dialysis treatment unit. For peritoneal dialysis (PD), the dialysis access site may be via a catheter. Hemodialysis (HD) treatment requires access to blood circulation in an extracorporeal circuit connected to the main cardiovascular circuit of the patient through a vascular or arteriovenous (AV) access. Typical HD access types may include arteriovenous fistula (AVF) and arteriovenous graft (AVG). During an HD treatment, blood is removed from the vascular access by an arterial needle fluidly connected to the extracorporeal circuit and provided to an HD treatment unit. After processing via the HD treatment unit, the blood is sent back to the vascular access through a venous needle and back into the patient cardiovascular circuit.

Accordingly, the health of the access site of a patient is of primary importance to the efficacy of the dialysis treatment. For example, a vascular access should be capable of providing a sufficient access blood flow (ABF) for HD treatment and should be free of serious complications, such as severe pain and/or swelling, stenosis, thrombosis, aneurysms, and/or the like. Thermal dilution is generally considered to be the most accurate ABF measurement technique. However, this is an invasive method that cannot typically be applied in a clinical routine. Doppler ultrasound (DU) is a non-invasive method that can be used to identify various access site characteristics, such as stenosis and thrombosis. However, DU requires a specifically trained operator. In addition, DU is time consuming and costly, which has prevented its wide-spread routine use. Accordingly, conventional access site monitoring techniques require specialized equipment and/or processes performed by trained, knowledgeable healthcare professionals, making them inefficient and cost-prohibitive.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In accordance with various aspects of the described embodiments, an apparatus may include at least one processor and a memory coupled to the at least one processor. The memory may include instructions that, when executed by the at least one processor, cause the at least one processor to generate video information based on a video of a dialysis access site of a patient, determine change in the number of pixels (CNP) information of the video information, the CNP information associated with movement of a skin surface of the patient due to blood flow through the dialysis access site, determine frequency domain information of the CNP information, determine a maximum-to-median power (M2) value of the frequency domain information, and determine at least one access site characteristic based on the M2 value.

In some embodiments of the apparatus, the at least one access site characteristic may include an access blood flow (ABF) rate. In various embodiments of the apparatus, the at least one access site characteristic may include an access site failure condition. In some embodiments of the apparatus, the instructions, when executed by the at least one processor, may cause the at least one processor to perform a regression analysis of the M2 value based on at least one patient characteristic to determine the at least one access site characteristic. In various embodiments of the apparatus, the instructions, when executed by the at least one processor, may cause the at least one processor to perform the regression analysis with access blood flow (ABF) rate as a dependent variable and the at least one patient characteristic as an independent variable.

In exemplary embodiments of the apparatus, the instructions, when executed by the at least one processor, may cause the at least one processor to determine M2 as $(MAX/MED)^2$, wherein MAX is a maximum waveform at a specific frequency in the frequency domain and MED is a median of all frequency ranges in the frequency domain. In various embodiments of the apparatus, the instructions, when executed by the at least one processor, may cause the at least one processor to determine CNP as a change of a characteristic of pixels in an area of interest in the video. In some embodiments of the apparatus, the characteristic may include one of color or intensity.

In various embodiments of the apparatus, the CNP information may include a time series of CNP. In exemplary embodiments of the apparatus, the instructions, when executed by the at least one processor, may cause the at least one processor to perform a time domain analysis of the video information via performing an amplitude analysis of the time series of CNP, and determining a peak point of the time series of CNP.

In accordance with various aspects of the described embodiments, a method may include generating video information based on a video of a dialysis access site of a patient, determining change in the number of pixels (CNP) information of the video information, the CNP information associated with movement of a skin surface of the patient due to blood flow through the dialysis access site, determining frequency domain information of the CNP information, determining a maximum-to-median power (M2) value of the frequency domain information, and determining at least one access site characteristic based on the M2 value.

In some embodiments of the method, the at least one access site characteristic may include an access blood flow (ABF) rate. In various embodiments of the method, the at least one access site characteristic may include an access site failure condition. In some embodiments of the method, the method may include performing a regression analysis of the M2 value based on at least one patient characteristic to determine the at least one access site characteristic. In various embodiments of the method, the method may include performing the regression analysis with access blood flow (ABF) rate as a dependent variable and the at least one patient characteristic as an independent variable.

In some embodiments of the method, the method may include determining M2 as $(MAX/MED)^2$, wherein MAX is a maximum waveform at a specific frequency in the frequency domain and MED is a median of all frequency ranges in the frequency domain. In various embodiments of the method, the method may include determining CNP as a change of a characteristic of pixels in an area of interest in the video. In exemplary embodiments of the method, the characteristic may include one of color or intensity.

In various embodiments of the method, the CNP information may include a time series of CNP. In some embodiments of the method, the method may include performing a time domain analysis of the video information via performing an amplitude analysis of the time series of CNP, and determining a peak point of the time series of CNP.

BRIEF DESCRIPTION OF THE DRAWINGS

By way of example, specific embodiments will now be described, with reference to the accompanying drawings, in which.

DETAILED DESCRIPTION

Figure 1:
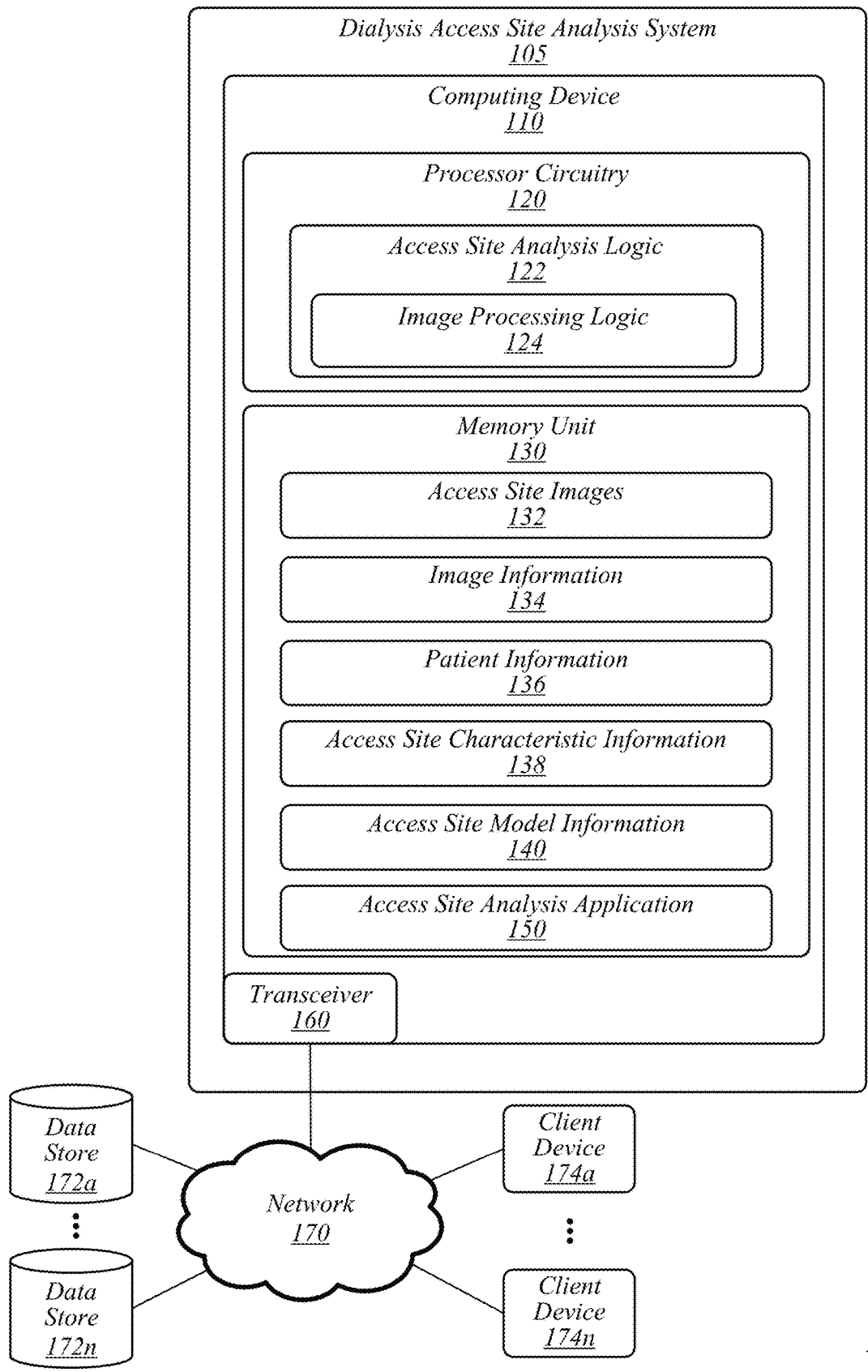
FIG. 1 illustrates a first exemplary operating environment in accordance with the present disclosure.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Dialysis treatment requires at least one dialysis access site for accessing the circulatory system of a patient. For example, hemodialysis (HD) may use an access site that includes an arteriovenous (AV) fistula (AVF), AV graft (AVG), or an HD catheter. An AVF is an artery surgically connected to a vein, while an AVG is a surgically placed conduit of synthetic material connecting an artery to a vein. For HD, AVF is the preferred modality.

In order to deliver enough blood through the extracorporeal circuit, the AVF must deliver an access blood flow (ABF) above a threshold rate, for example, several hundred milliliters (mL) per minute. In certain patients, such as chronic kidney disease (CKD) and/or end-stage renal disease (ESRD) patients, a sufficient ABF is often hindered by the development of access site complications, including AVF stenosis and thrombosis. Such complications may lead to inadequate ABF and/or AVF failure. Patients who develop AVF failure may be required to undergo various types of vascular intervention, which adds burden and costs to the patient, as well as the potential to introduce new health risks.

ABF monitoring and pre-emptive repair of sub-clinical AVF stenosis has been shown to reduce the rate of thrombosis and other complications and prolong the functional life of mature AVFs. For example, the measurement of ABF may be used to assess the development of AVF stenosis and other complications. As described above, thermal dilution is generally considered to be the most accurate ABF measurement technique. However, thermal dilution is an invasive method that cannot typically be applied in a typical HD clinical setting. Doppler ultrasound (DU) is a non-invasive method that can be used to identify various access site characteristics, such as stenosis and thrombosis. However, DU requires specialized equipment and a trained, knowledgeable operator in order to be effective. In addition, DU is time consuming and costly, which has prevented its wide-spread routine use. Accordingly, conventional access site monitoring techniques require specialized equipment and/or processes performed by trained, knowledgeable healthcare professionals, making them inefficient, inconvenient, and cost-prohibitive.

Accordingly, some embodiments provide an access site analysis process operative to perform a non-invasive, contact-free, and easy-to-use technique that may allow the clinical staff, the patient, and/or a caregiver to assess access site characteristics, including AVF ABF, stenosis, thrombosis, and/or the like. In some embodiments, the access site analysis process may access a plurality of images (for instance, a video) of an access site of the patient. For example, a patient or caregiver may take a video of the AVF region of the patient using a smartphone or other computing/imaging device and provide the video to an access site analysis system. A region of interest (ROI) in the video may be analyzed to determine changes in the number of pixels (CNP) of elements or portions of the access site over the course of time, such as over successive frames of a video. The CNP information may indicate access site motion, for instance, AVF motion due to ABF through AVF. For example, the greater the change in CNP, the greater the motion of the AVF and, therefore, the greater the ABF, and vice versa.

The access site analysis process may convert the CNP information into a time series that may be transferred to the frequency domain, for instance, via a Fourier transfer process. The frequency domain information may be analyzed to determine a maximum waveform at a specific frequency in the frequency domain (MAX) and the median of all frequency ranges (MED). The MAX and MED may be used to determine the maximum-to-median power (M2) via calculating the square of the ratio of MAX to MED: $M2=(MAX/MED)^2$. In some embodiments, access site information may include historical or model information indicating access site characteristics associated with various M2 values or ranges of values. The access site information may be patient-specific and/or population-specific. The M2 determined for a patient may be compared with the model information to determine at least one access site characteristic. For example, for Patient A, an M2 value of X may correlate to an estimated ABF of Y (for example, determined directly or via further processing, such as a regression analysis). In another example, for Patient B, an M2 value below a threshold may indicate complication Z (for instance, thrombosis). Embodiments are not limited in this context.

In some embodiments, the access site analysis process may be used to remotely monitor, analyze, trend, and/or the like a patient's access site by using a combination of digital imaging, trending, intervention and outcome information to improve the longevity and care of a patent and their access site. In some embodiments, the access site analysis process may be an internet-based, Software-as-a-Service (SaaS), and/or cloud-based platform that may be used by a patient or a healthcare team to monitor patients clinical care and can be used to provide expert third-party assessments, for example, as a subscription or other type of service to healthcare providers.

For example, the access site analysis process may operate in combination with a "patient portal" or other type of platform that a patient and healthcare team may use to exchange information. For instance, dialysis treatment centers mange in-home patients who receive treatment in their own home and in-center patients who receive treatment at a treatment center. In-home patients may take a video of their access site, such as an AVF site, AVG site, and/or the like, using a smartphone or other personal computing device on a periodic basis (for instance, daily, weekly, monthly, and/or the like) or as necessary (for instance, based on the appearance and/or change in the condition of the access site). A video of an access site may include skin in the area adjacent, proximal, in contact with, or otherwise associated with the access site. The video may be uploaded to a patient portal or other platform and routed to a dialysis access site analysis system operative to perform the access site analysis process according to some embodiments. Similarly, videos of the access sites of in-center patients may be taken by the patient and/or clinical staff and uploaded to the patient portal for access by the access site analysis system.

In some embodiments, patient videos may be stored in a repository or other database, including, without limitation, a healthcare information system (HIS), electronic medical record (EMR) system, and/or the like. Videos in the repository may be catalogued and indexed by patient including key clinical information, demographics, medical history, and/or the like to be processed by the access site analysis system at a patient level and/or a population level. Use of patient image information, for example, at a population-level, may require de-identification of protected health information (PHI) and/or other information capable of identifying a patient according to required regulations, protocols, and/or the like, such as Health Insurance Portability and Accountability Act of 1996 (HIPAA).

In some embodiments, the access site analysis system may provide an assessment or diagnosis and/or one or more treatment recommendations based on the M2 value determined based on the access site video, which may be provided to a healthcare team. The healthcare team may then review the recommendations and either accept, decline, or revise the intervention for the patient. Healthcare team interventions may be documented and stored in the repository on both a patient-level and a population-level so that they can be followed to monitor success rates and outcomes to provide further training data to computational models used according to some embodiments.

Therefore, dialysis access site analysis processes according to some embodiments may provide multiple technological advantages and technical features over conventional systems, including improvements to computing technology. One non-limiting example of a technological advantage may include examining access sites using automated processes of digital videos employing, for example, artificial intelligence (AI) and/or machine learning (ML) processes. Another non-limiting example of a technological advantage may include allowing remote analysis of a patient access site without requiring an in-person visual inspection and/or specialized test (for instance, thermal dilution, DU, and/or the like) by a healthcare professional, reducing or even eliminating the need for a visit to/from the healthcare professional by/to the patient. In a further non-limiting example of a technological advantage, access site analysis processes according to some embodiments may operate to generate an access site diagnosis (for instance, healthy, thrombosis, and/or the like) using an M2 value determined from video information. Other technological advantages are provided in this Detailed Description. Embodiments are not limited in this context.

FIG. 1 illustrates an example of an operating environment 100 that may be representative of some embodiments. As shown in FIG. 1, operating environment 100 may include a dialysis access site analysis system 105. In various embodiments, dialysis access site analysis system 105 may include a computing device 110 communicatively coupled to network 170 via a transceiver 160. In some embodiments, computing device 110 may be a server computer or other type of computing device.

Computing device 110 may be configured to manage, among other things, operational aspects of an access site analysis process according to some embodiments. Although only one computing device 110 is depicted in FIG. 1, embodiments are not so limited. In various embodiments, the functions, operations, configurations, data storage functions, applications, logic, and/or the like described with respect to computing device 110 may be performed by and/or stored in one or more other computing devices (not shown), for example, coupled to computing device 110 via network 170 (for instance, one or more of client devices 174a-n). A single computing device 110 is depicted for illustrative purposes only to simplify the figure. Embodiments are not limited in this context.

Computing device 110 may include a processor circuitry that may include and/or may access various logics for performing processes according to some embodiments. For instance, processor circuitry 120 may include and/or may access an access site analysis logic 122 and/or image processing logic 124. Processing circuitry 120, access site analysis logic 122, image processing logic 124, and/or portions thereof may be implemented in hardware, software, or a combination thereof. As used in this application, the terms "logic," "component," "layer," "system," "circuitry," "decoder," "encoder," "control loop," and/or "module" are intended to refer to a computer-related entity, either hardware, a combination of hardware and software, software, or software in execution, examples of which are provided by the exemplary computing architecture 1100. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a computational model or application, an AI model or application, an ML model or application, a proportional-integral-derivative (PID) controller, variations thereof, combinations of any of the foregoing, and/or the like.

Although access site analysis logic 122 is depicted in FIG. 1 as being within processor circuitry 120, embodiments are not so limited. For example, access site analysis logic 122, image processing logic 124, and/or any component thereof may be located within an accelerator, a processor core, an interface, an individual processor die, implemented entirely as a software application (for instance, an access site analysis application 150) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store various types of information and/or applications for an access site analysis process according to some embodiments. For example, memory unit 130 may store access site images 132, image information 134, patient information 136, access site characteristic information 138, access site model information 140, and/or an access site analysis application 150. In some embodiments, some or all of access site images 132, image information 134, patient information 136, access site characteristic information 138, access site model information 140, and/or an access site analysis application 150 may be stored in one or more data stores 172a-n accessible to computing device 110 via network 170. For example, one or more of data stores 172a-n may be or may include a HIS, an EMR system, a dialysis information system (DIS), a picture archiving and communication system (PACS), a Centers for Medicare and Medicaid Services (CMS) database, U.S. Renal Data System (USRDS), a proprietary database, and/or the like.

In some embodiments, access site analysis logic 122, for example, via image processing logic 124 and/or access site analysis application 150, may operate to analyze access site images 132 of access sites to determine access site characteristics, such as ABF and/or the presence of access site conditions, such as thrombosis. Access site images 132 may be or may include an electronic file that includes a picture and/or video of an access site and/or other portions of a patient. The images may be stored as image or video files such as *.mp3, *.mp4, *.avi, *.jpg, *.png, *.bmp, *.tif, and/or the like. In some embodiments, the access site images 132 may include a video of an access site taken over an image time period (for instance, about 60 seconds to about 120 seconds). In other embodiments, the access site images 132 may include a series of successive images taken over an image time period at successive intervals, such as about every 5 seconds to about every 5 minutes.

In various embodiments, image processing logic 124, for example, via access site analysis application 150, may operate to process images to generate image information 134. In reference to a video, image information 134 may be or may include video information. In general, image information 134 may include any information that may be obtained or determined from access site images 132. Non-limiting examples of image information may include color information, intensity information, motion information, and/or the like. For example, image information may include information associated with changes between frames of a video, such as variation in color, intensity, CNP, and/or the like.

In addition, image information 134 may include information resulting from processing of an image, video, frame, and/or other image information 134 by image processing logic 124. For example, all or some of the motion exhibited by an access site, such as an AVF, may be difficult if not impossible to see with the human eye from raw image data. In some embodiments, access site motions may be amplified to increase the scale of the motion to simplify the delineation between noise and movement in the video. The motion amplification may be achieved by, for example, performing Eulerian video magnification on the captured video. In some embodiments, Eulerian video magnification may be performed according to one or more of the methods and/or variations thereof described in Wu et al., "Eulerian Video Magnification for Revealing Subtle Changes in the World," ACM Trans. Graph. Vol. 31, pp. 1-8, 2012; U.S. Patent Application Publication No. 2014/0072190, entitled "Linear-Based Eulerian Motion Modulation," and/or U.S. Patent Application Publication No. 2017/0119258, entitled "Method and Apparatus of Assessment of Access Flow in Hemodialysis Patients by Video Imaging Processing," all of which are incorporated by reference as if fully set forth herein.

In another example, image information 134 may include transformations of data generated based on access site images 132, including, without limitation, linear transforms, time series or domain information, frequency domain information/graphs (see, for example, FIG. 4), CNP, M2 information, regression analysis information, and/or the like. Embodiments are not limited in this context.

A patient, healthcare provider, caretaker, or other individual may capture access site images (or videos) 132 using any capable device, such as a smartphone, tablet computing device, laptop computing device, personal computer (PC), camera, digital camera, video camera, and/or the like. A user, such as the patient and/or healthcare professional, may send, transmit, upload, or otherwise provide access site videos 132 to access site analysis system 105 via a client device 174a communicatively coupled to computing device 110 via network 170. For example, access site analysis application 150 may be or may include a website, internet interface, portal, or other network-based application that may facilitate uploading digital access site videos 132 for storage in memory unit 130 and/or data stores 172a-n. In some embodiments, a patient client device 174a-n may operate a client application (for instance, a mobile application or "app") operative to communicate with access site analysis application 150 for providing access site videos 132. In some embodiments, a patient may upload digital access site videos 132 via a patient portal of a dialysis clinic or other healthcare provider. Access site analysis application 150 may be communicatively coupled to the patient portal to receive images therefrom. Embodiments are not limited in this context.

In addition, a patient or healthcare provider may provide image information 134 describing characteristics of the access site. In general, image information 134 may include any type of textual, audio, visual, and/or the like data outside of an access site video 132 that may indicate characteristics of the access site. For example, image information 134 may include descriptions regarding day/time of video capture, pain, swelling, color, size, ABF information, duration of a condition or characteristic, age of access site, type of access site, patient vitals, and/or the like. In various embodiments, image information 134 may be associated with one or more access site videos 132, for example, as metadata, related within one or more medical record entries, and/or the like. For instance, access site analysis application 150 may create a record for an access site video 132 that includes or refers to associated image information 134. In this manner, access site analysis application 150 may access information describing and/or providing context to an access site video 132 (for instance, a record for Patient Video 1 for Patient A, indicating that the patient has had the AVF for X months and has had thrombosis for Y weeks).

In some embodiments, patient information 136 may include information associated with a patient corresponding to an access site video 132. Non-limiting examples of patient information 136 may include name and address information, patient identifiers, dialysis information, prescription information, medical conditions, healthcare provider information, access site information, and/or the like. In some embodiments, patient information 136 may include access site images 132 associated with the patient, for instance, as part of a medical record. Embodiments are not limited in this context.

Access site analysis application 150 may analyze access site images 132 and/or image information 134 to determine access site characteristic information 138. In general, access site characteristic information 138 may include a diagnosis, classification, categorization, access site features, or other analysis result determined from analyzing an access site image 132 and/or image information 134. For example, access site characteristic information 138 may include access site features of an access site image 132, including, without limitation, blood flow information (for instance, ABF), color, size, shape, access site elements (for instance, scabbing, bleeding, and/or the like), and/or other information that may be discerned from analyzing an access site image 132. In some embodiments, access site characteristic information 138 may include an estimated ABF value or rate (for instance, X ml/min). In various embodiments, access site characteristic information 138 may include a diagnosis or other classification of an access site, such as a healthy diagnosis, a grade or other classification level, indication of the presence and/or severity of an abnormality or failure (for instance, thrombosis), and/or the like.

In some embodiments, access site analysis application 150 may use access site model information 140 to determine access site characteristic information 138. In general, access site model information 140 may be or may include historical information of the patient and/or a patient population that may be used to determine access site characteristic information 138. For example, access site model information 140 may include M2 values of a population of patients. As described in more detail herein, access site analysis application 150 may determine an M2 value for the patient via analyzing an access site video 132. Access site analysis application 150 may lookup the M2 value in a lookup table, computational model, database, and/or the like to determine an ABF rate corresponding to the M2 value. For example, Video 1 of Patient A may be determined to have an M2 value of X, which corresponds to an ABF rate of Y ml/min. In another example, Video 2 of Patient B may be determined to have an M2 value of T, which corresponds to an ABF rate of U ml/min based on M2 values of a patient population having characteristics that correspond to Patient B.

In some embodiments, access site model information 140 may include a computational model for determining access site characteristic information 138 (for instance, ABF rates) based on image information 134 (for instance, M2 values) and/or patient information 136. For example, an AI and/or ML model may be used to determine an ABF rate for a patient corresponding to a determined M2 value and patient characteristics. In various embodiments, access site model information 140 may include models specifically for analyzing images. For example, an AI and/or ML model may be trained to determine image information 134, such as CNP, via analyzing an access site video 132. Non-limiting examples of computational models may include an ML model, an AI model, a neural network (NN), an artificial neural network (ANN), a convolutional neural network (CNN), a deep learning (DL) network, a deep neural network (DNN), a recurrent neural network (RNNs), combinations thereof, variations thereof, and/or the like. Embodiments are not limited in this context.

Figure 2:
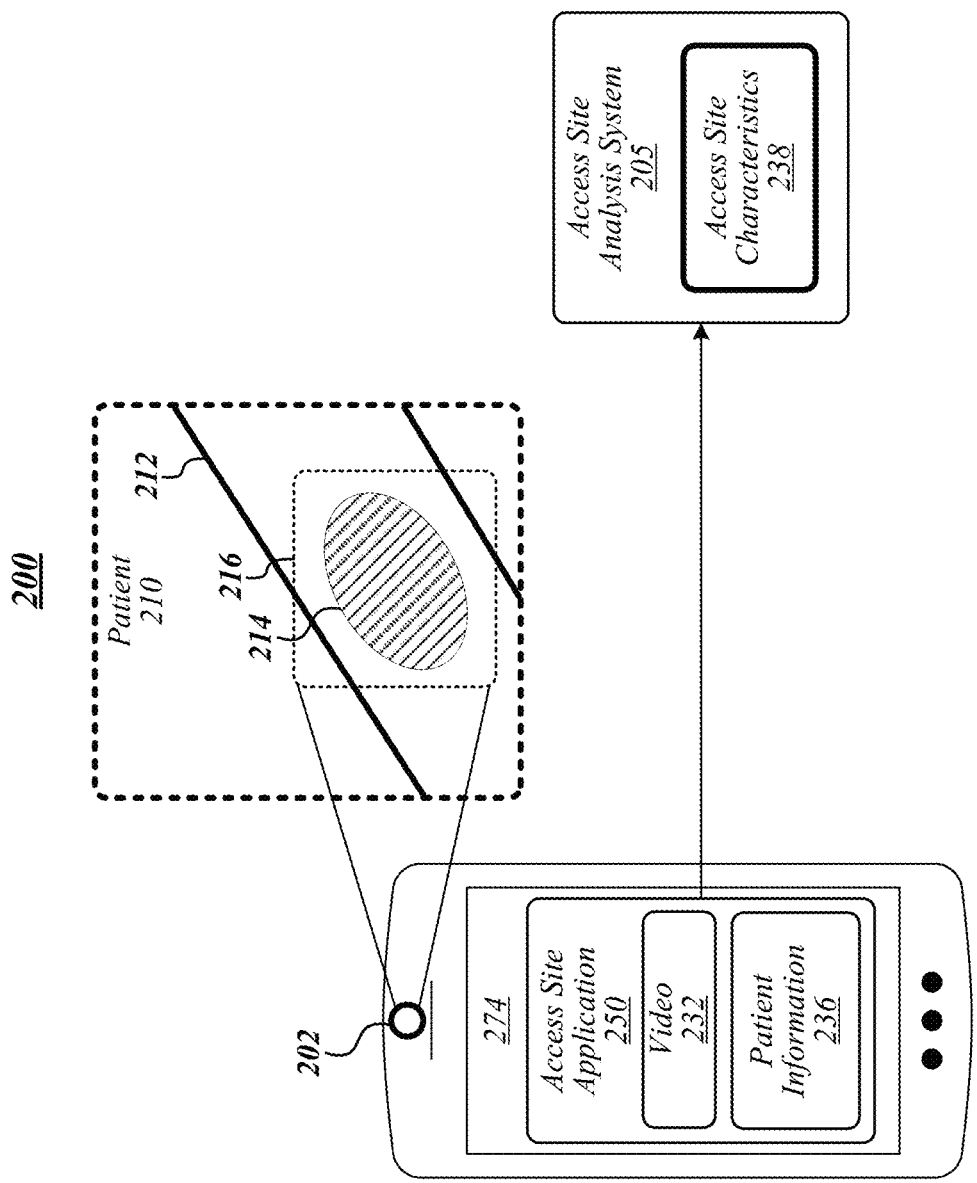
FIG. 2 illustrates a second exemplary operating environment in accordance with the present disclosure.

FIG. 2 illustrates an example of an operating environment 200 that may be representative of some embodiments. As shown in FIG. 2, operating environment 200 may include a patient computing device 274, such as a smartphone, a tablet computing device, a portable computing device, and/or the like. Computing device 274 may execute an access site application 250. In some embodiments, access site application 250 may be or may include a mobile application, client application, web-based application, email application and/or the like for interacting (for instance, directly or via a patient portal) with a dialysis access site analysis system 205 configured according to various embodiments.

A user may capture or otherwise access a video 232 of an access site or other portion of the patient. For example, a user may take one or more pictures and/or a video of the access site via camera 202 (see, for instance, FIG. 7). A user may capture video 232 of an area 216 of a portion 212 of patient 210, such as an arm 212 portion having a target area 214. In some embodiments, target area 214 may be an area targeted for videoing that may indicate blood flow according to some embodiments. In various embodiments, target area 214 may include all or some of an access site. In other embodiments, target area 214 may include an area completely or partially outside of the access site, such as an area above the access site, below the access site, to the side of the access site, or otherwise adjacent to the access site. Accordingly, reference to a video or still image of an access site herein may refer to include video images of all, some, or none of an access site and/or all, some, or none of an area (for instance, skin) above, below, besides, or otherwise adjacent to an access site. Embodiments are not limited in this context.

Area 216 on patient 210 may have various dimensions. For example, patient 210 may capture video 232 of an area about 10 cm in length and 5 cm wide. In various embodiments, area 216 may have a length and/or width of about 1 cm, about 2 cm, about 5 cm, about 10 cm, about 15 cm, about 20 cm, and any value or range between any two of these values (including endpoints). Camera 202 may capture video 232 at an image distance from portion 212, such as about 1 cm, about 2 cm, about 5 cm, about 10 cm, about 15 cm, about 20 cm, about 25 cm, about 30 cm, and any value or range between any two of these values (including endpoints). Video 232 may be captured for an image or video time period. In various embodiments, video time period may be about 5 seconds, about 10 seconds, about 30 seconds, about 1 minute, about 2 minutes, about 5 minutes, about 10 minutes, about 30 minutes, about 1 hour, and any value or range between any two of these values (including endpoints). In some embodiments, video 232 may be captured at a resolution of below about 720 p, about 720 p, below about 1080 p, about 1080 p, above about 1080 p, and any value or range between any two of these values (including endpoints). In exemplary embodiments, video 232 may be captured at various frame speeds, such as about 10 frames-per-second (fps), about 20 fps, about 30 fps, about 50 fps, and any value or range between any two of these values (including endpoints). In general, the size of area 216, the image distance, the image time period, the resolution, the frame speed, and/or any other video characteristics may be of sufficient values to capture access site 214 for analysis according to some embodiments.

In some embodiments, access site application 250 may allow a user to enter patient information 237 describing video 232 and/or other personal characteristics. In some embodiments, access site application 250 may provide text boxes, check boxes (for example, to indicate the presence of a condition), selection objects, or other graphical user interface (GUI) objects for entering patient information 236, including access site description information. In some embodiments, access site application 250 may facilitate the capture of video 232. For example, a user may open access site application 250 and access site application 250 may provide an image capture function (for instance, using camera 202 and/or display screen of computing device 274), such as providing a target area or bounding box to be placed around access site 214 for proper video capture of access site 214.

Video 232 may be uploaded or otherwise made available to access site system 205 according to some embodiments, along with other information, such as patient information 236, image information (for instance, patient description of the image, camera information, resolution information, raw image data, and/or the like). In various embodiments, video 232 may be transmitted to access site analysis system 205 associated with patient information 236, image information, and/or the like, for instance, as a record or other data structure. In various embodiments, access site analysis system 205 may process video 232 according to some embodiments to generate access site characteristics 238 such as, for example, an ABF estimate.

Figure 3:
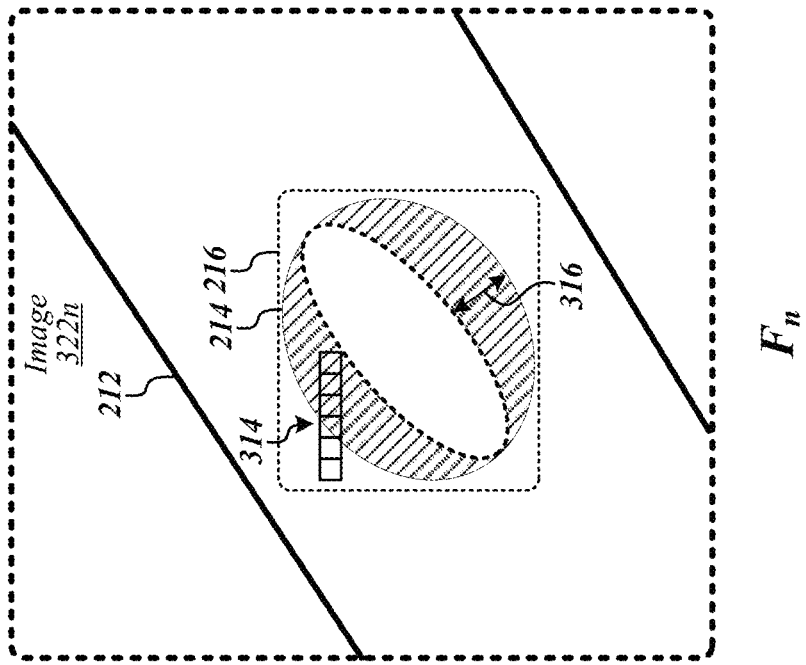
FIG. 3 illustrates images of an access site in accordance with the present disclosure.
Figure 3:
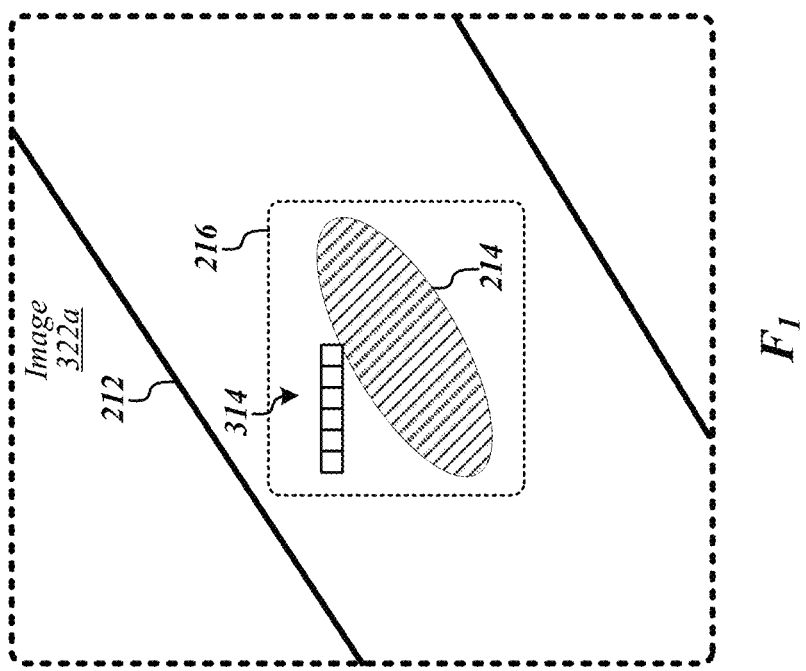

FIG. 3 illustrates images of an access site in accordance with the present disclosure. For example, image 322*a* may be a first frame ($F_1$) and image 322*n* may be a subsequent frame ($F_n$) of a video. Image 322*n* may be a certain amount of time after image 322*n*, depending on the frame speed (i.e., fps) and/or the amount of time between image analyses by access site analysis process (for example, about 10 milliseconds, about 50 milliseconds, about 1 second, about 2 seconds, about 5 seconds, about 10 seconds, about 30 seconds, about 1 minute, about 2 minutes, about 5 minutes, and any range or value between any two of these values (including endpoints)). Images 322*a-n* may be images of an area 216 of a portion 212 of a patient, for example, including an access site 214 and skin surrounding or adjacent to access site. In some embodiments, area 216 may be a region of interest (ROI), a bounding box, or other visual element. In other embodiments, area 216 may not be a part of image. In some embodiments, successive frames may be analyzed. In other embodiments, frames at various intervals (for instance, every X frames) may be analyzed.

Access site analysis process may determine access site 214 in images 322*a*. In various embodiments, access site analysis process, for example, via image processing logic, may determine change in the number of pixels (CNP) of access site 214 between images. In general, CNP may determine a change in the number of pixels with respect to a characteristic of the pixels, such as a visual property of the pixels. Non-limiting examples of a visual property may include color, intensity, and/or the like. For example, determining CNP may include determining, pixel-by-pixel, a plurality of intensity differences between each pixel (or each pixel in an area of interest) in consecutive frames.

As shown in FIG. 3, the size of an area associated with access site 214 may increase between image 322*a* and image 322*n*. The increase in the area may be due to various characteristics associated with the function of access site 214, for example, due to fluid dynamics beneath the skin of access site 214 and/or adjacent to access site 214. For example, blood flow may change the color of the skin of access site 214 and/or adjacent to access site 214; blood flow may change the size of access site 214 and/or an opening thereof; blood flow may cause motion of access site 214 and/or skin adjacent to access site (i.e., access site 214 and/or skin adjacent to access site 214 may be displaced, flex, or pulsate based on blood flow); combinations thereof, and/or the like. The changes in the physical characteristics of access site 214 and/or physical characteristics skin that is a part of or adjacent to access site 214 may be detectable via determining changes in pixels of images of access site and/or skin that is a part of or adjacent to access site. For example, the sequence of frames F1-Fn of images 232*a-n* may capture motion by the skin in the area of interest as illustrated by AV fistula motion 316. In another example, the sequence of frames F1-Fn of images 232*a-n* may capture changes in the color of or other changes in a characteristic of the skin in the area of interest as illustrated by AV fistula motion 316

Referring to image 322*n*, therein is depicted access site 214 that has increased in size or a characteristic (for instance, a skin color) that has changed in size (the dotted portion within access site 214 of image 322*n* is access site 214 in image 322*a* to show the increase in size). For example, with a pulse of blood flow, the color of skin of access site 214 and/or adjacent to access site 214 may change in color and/or intensity of color (which may not be perceptible to the human eye). The rate of blood flow may be related to the amount of change of pixels in images 322*a-n*. For example, (the patterned area of) access site 214 in image 322*a* may be, for example, a certain intensity of a color or color of interest (red, for example, when amplified). An illustrative set of pixels 314 in image 322*a* are not colored (or are below a threshold intensity). In image 322*n*, the red color and/or intensity thereof has increased in area, such that 4 of the set of pixels 314 are now red. Accordingly, between images 322*a* and 322*n*, a CNP of 4 has occurred. The CNP may be determined based on various characteristics, such as pixels changing from one color (i.e., normal skin color of the patient) to another (i.e., a color generated when blood flows through access site) and/or changes in intensity from a first intensity (below a threshold) to a second intensity (above a threshold), affected by blood flow through access site. As described in more detail herein, the CNP may be related to the rate of blood flow (for instance, ABF rate). For example, the greater the blood flow rate, the greater CNP, and vice versa. In another example, an amount or pattern of CNP may indicate an access site failure.

The motion exhibited by the skin based on various fluid dynamics beneath the skin due to blood flow may be very small. Amplifying the small motion exhibited by the skin according to some embodiments better enables delineation between noise and motion in the video that is attributable to the movement of the skin. Any of a variety of methods may be employed to amplify the motion in the captured video, for example, as described in U.S. Patent Application Publication No. 2014/0072190, entitled "Linear-Based Eulerian Motion Modulation," and/or U.S. Patent Application Publication No. 2017/0119258, entitled "Method and Apparatus of Assessment of Access Flow in Hemodialysis Patients by Video Imaging Processing." Embodiments are not limited in this context. For example, other image processing techniques may be employed to obtain video information from images 322*a-n*.

Accordingly, in some embodiments, movement of the skin surfaces of access site and/or adjacent to access site induced by ABF may be determined by quantitation of the frame-to-frame changes in CNP. In some embodiments, CNP from a sequence of image frames in a digital video may be transferred to a time series, for example, as described in Nakajima et al. "Detection of Apparent Skin Motion Using Optical Flow Analysis: Blood Pulsation Signal Obtained from Optical Flow Sequence," Rev. Sci. Instrum. Vol. 68, pp. 1331-1336, 1997 and/or Zhu et al., "Estimation of Arterio-Venous Access Blood Flow in Hemodialysis Patients Using Video Image Processing Technique," Conf Proc IEEE Eng Med Biol Soc. pp: 207-210, 2016. This time series can then be transferred into the frequency domain for example, via applying fast Fourier transform (FFT) to the time series. In this signal, sample frequency (Fs) is the frame per second (fps) and time is total number of frames divided by Fs. The variation of baseline of signal in time series may be associated with patient physical characteristics, such as skin color. Accordingly, adjustments may be performed to adjust the baseline based on patient characteristics, such as skin color, skin tone, race, and/or the like.

Figure 4:
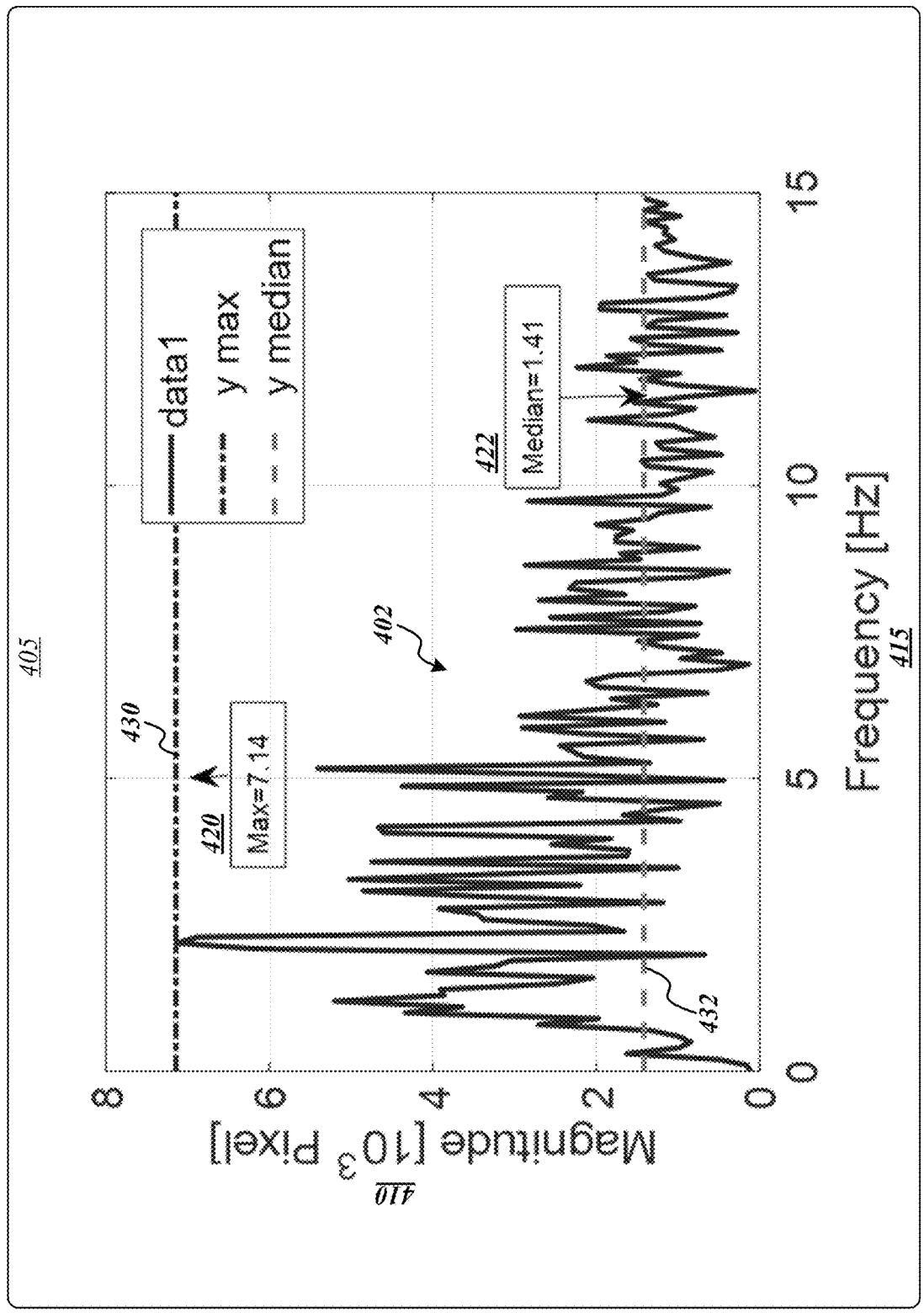
FIG. 4 illustrates a graph of frequency domain information in accordance with the present disclosure.

FIG. 4 illustrates a graph of frequency domain information in accordance with the present disclosure. As shown in FIG. 4, video information from a video of an access site may be transformed via image processing into a frequency domain. Graph 405 depicts frequency 415 vs. magnitude 410. In various embodiments, the change in the amplitude in main components or its ratio in the frequency domain may correlate with the change in ABF. For example, the frequency domain information may be analyzed to determine a maximum waveform at a specific frequency in the frequency domain (MAX) and the median of all frequency ranges (MED). The MAX and MED may be used to determine the maximum-to-median power (M2) via calculating the square of the ratio of MAX to MED: $M2=(MAX/MED)^2$. In various embodiments, M2 may be used as a predictor of ABF in regression models. For example, regression models with ABF as the dependent variable may include, without limitation, as independent variables one or more of M2, age, race, and weight.

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation. Blocks designated with dotted lines may be optional blocks of a logic flow.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 5:
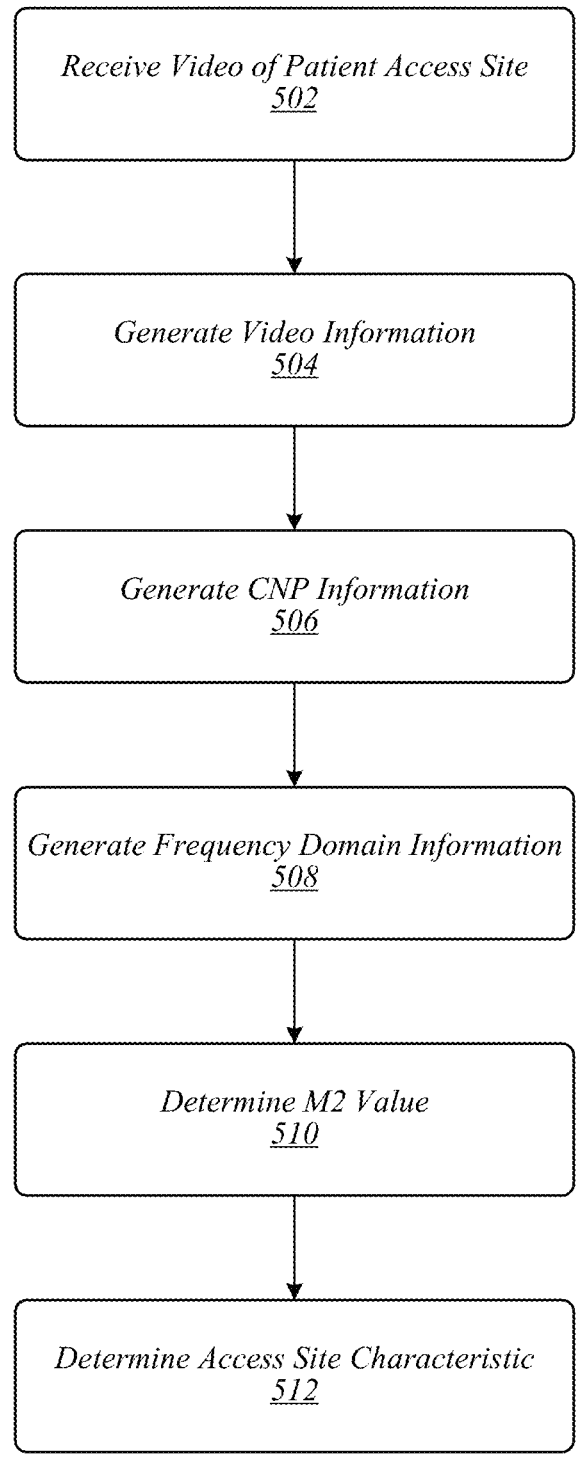
FIG. 5 illustrates a first logic flow in accordance with the present disclosure.

FIG. 5 illustrates an embodiment of a logic flow 500. Logic flow 500 may be representative of some or all of the operations executed by one or more embodiments described herein, such as computing device 110. In some embodiments, logic flow 500 may be representative of some or all of the operations of an access site analysis process according to some embodiments.

At block 502, logic flow 500 may receive a video of a patient access site. For example, an access site analysis system may receive a video of an access site (and surrounding or adjacent skin) of a patient. Logic flow 500 may generate video information at block 504. For example, an image processing logic may analyze characteristics of pixels in frames of the video to determine information such as color information, intensity information, and/or the like for pixels within the frames. At block 506, logic flow 500 may generate CNP information. For example, CNP may be determined based on the video information indicating a change in a characteristic of pixels. For example, CNP may include a count or other measurement of pixels experiencing a change from a first color to a second color, a change from a first intensity to a second intensity, falling below an intensity threshold, going above an intensity threshold, and/or the like. Embodiments are not limited in this context. In general, the pixel factors for determining CNP may include factors that are associated with determining access site blood flow characteristics.

Logic flow 500 may generate frequency domain information at block 508. For example, the CNP information may be converted to a time series. The time series may be converted to the frequency domain, for example, via a Fourier analysis, such as FFT. Graph 405 of FIG. 4 illustrates an example of frequency domain information according to some embodiments. At block 510, logic flow 500 may determine an M2 value. For example, the frequency domain information may be analyzed to determine a maximum waveform at a specific frequency in the frequency domain (MAX) and the median of all frequency ranges (MED). The MAX and MED may be used to determine the maximum-to-median power (M2) via calculating the square of the ratio of MAX to MED: $M2=(MAX/MED)^2$.

At block 512, logic flow 500 may determine an access site characteristic. For example, M2 may be used to look up an ABF rate in a lookup table and/or provided to a computational model to determine an ABF rate that corresponds to the M2 value (and any associated patient information). In various embodiments, M2 may be used as a predictor of ABF in regression models. For example, regression models with ABF as the dependent variable may include, without limitation, as independent variables one or more of M2, age, race, and weight.

In some embodiments, determining an access site characteristic may include a diagnosis of an access site, such as an access site failure (for instance, stenosis). For example, the ABF may be used as an indicator and/or predictor of an access site failure (alone or in combination with other factors, such as the physical condition of the access site).

Figure 6:
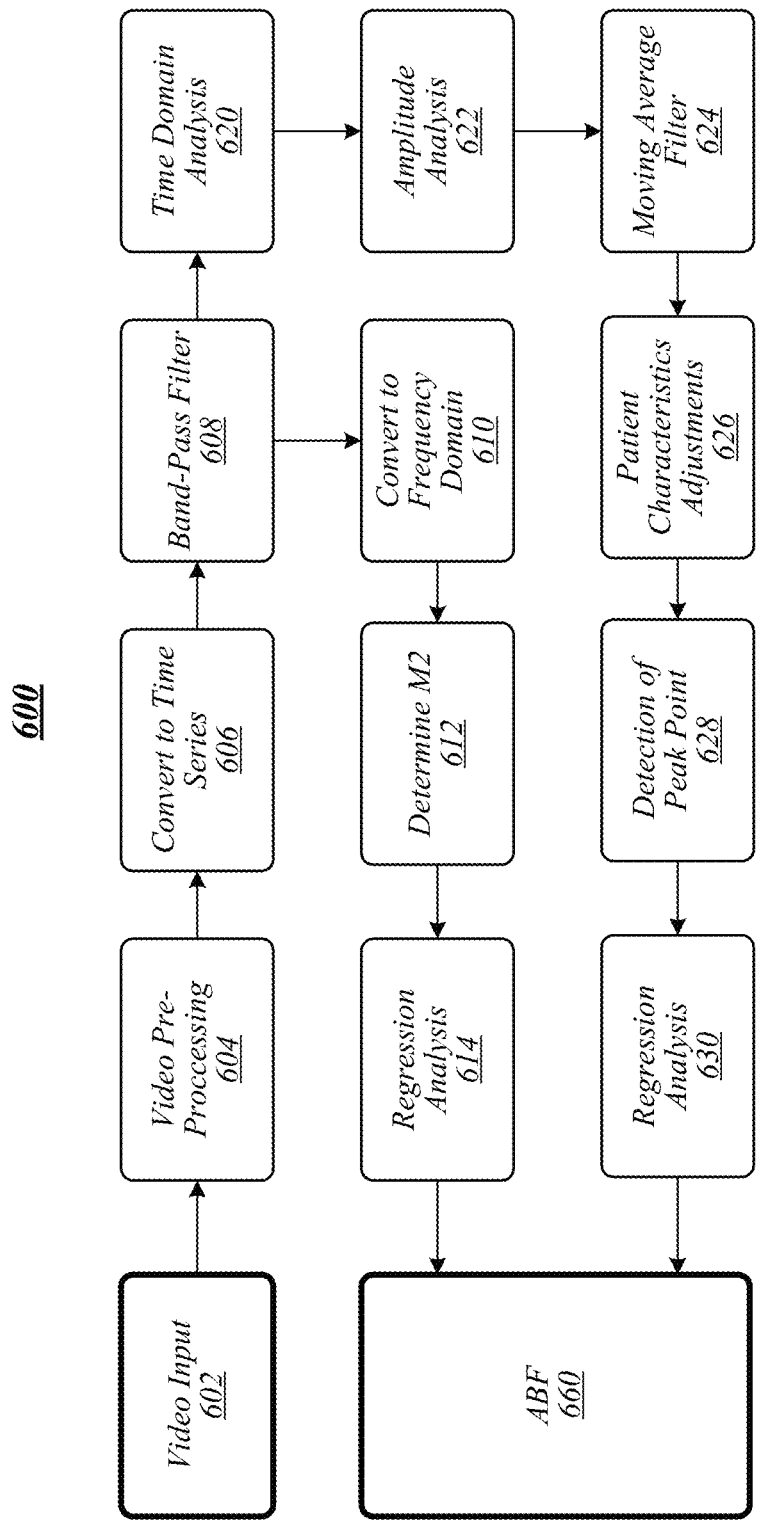
FIG. 6 illustrates a second logic flow in accordance with the present disclosure.

FIG. 6 illustrates an embodiment of a logic flow 600. Logic flow 600 may be representative of some or all of the operations executed by one or more embodiments described herein, such as computing device 110. In some embodiments, logic flow 600 may be representative of some or all of the operations of an access site analysis process according to some embodiments.

At block 602, logic flow 600 may receive video input. For example, a patient or healthcare professional may capture a video of a portion of the patient including an access site and surrounding skin. The video may be uploaded as a digital file to an access site analysis system configured according to some embodiments. Logic flow 600 may perform pre-processing at block 604. For example, the video may be processed to improve the signal-to-noise ratio, magnify or amplify relevant features (for instance, via Eulerian video magnification), and/or the like.

Logic flow 600 may convert the video to a time series at block 606. For example, an access site analysis process may convert the video to video information that includes a signal including a time series based on CNP between consecutive frames. For example, CNP for pixels in the video may be determined for a pixel characteristic, such as a color value or intensity. A time series may be determined for the CNP for the pixel characteristic over time as determined by analyzing frames of the video. At block 608, logic flow 600 may apply a band-pass filter to the time series video information. For example, the motion of interest may have a limited possible range of frequency values. Accordingly, signal components with frequency values above/below the range of interest are likely noise and may be excluded. In the example of a video of an AVF, the range of interest may be between a low threshold and a high threshold and a bandpass filter may be constructed that attenuates signal components, for example, below about 0.02 Hz (low threshold) and above about 2 Hz (high threshold). In some embodiments, the low threshold may be about 0.01 Hz to about 1 Hz and the high threshold may be about 2 Hz to about 10 Hz.

Logic flow 600 may take different paths to obtain an ABF value at block 660 or other determinations (for instance, an access site condition, such as an access site failure). A first path may include a "frequency domain" path starting at block 610. A second path may include a "time domain" or "amplitude" path starting at block 622. In some embodiments, an access site failure may be determined or predicted by a combination of time domain and frequency domain analysis. For example, regression analysis may be performed by two indepenent variables, the M2 in frequency domain and the amplitude in time domain to fit the dependent varible of degree of stenosis or other access problem.

At block 610, logic flow 600 may convert the time series to the frequency domain. For example, FFT may be applied to the time series at a specified interval to produce the frequency domain signals. For example, the specified interval may be about every 10 seconds. In other examples, the specified time interval may be about every 1 second, about every 2 seconds, about every 5 seconds, about every 10 seconds, about every 30 seconds, about every 60 seconds, and any value or range between any two of these values (including endpoints). Logic flow 600 may determine M2 from the frequency domain information at block 612. For example, frequency domain information may be video information generated from a video as plotted in graph 405 of FIG. 4. The frequency domain information may be analyzed to determine a maximum waveform at a specific frequency in the frequency domain (MAX) and the median of all frequency ranges (MED). The MAX and MED may be used to determine the maximum-to-median power (M2) via calculating the square of the ratio of MAX to MED: $M2=(MAX/MED)^2$.

At block 614, logic flow 600 may perform a regression analysis. For example, one or more regression analyses based on one or more of the independent variables of M2, age, gender, and/or race and dependent variable of ABF may be performed. In some embodiments, ABF dependent variable information may be determined via a standardized, conventional process, such as a thermal dilution method (for instance, performed using a HVT100 endovascular flowmeter provided by Transonic® of Ithaca, N.Y., United States). Logic flow 600 may determine an estimated ABF rate based on the regression analysis at block 660.

At block 622, logic flow 600 may perform an amplitude analysis. For example, the time domain signal may include a waveform of CNP over time (or frames). The analysis of the amplitude of the waveform may provide changes in volume and pressure of the blood associated with the access site, such as access vessels. Logic flow 600 may perform a moving average filter at block 624. For example, a moving average filter may be applied to reduce the intervention from turbulent flow in the access site. At block 626, logic flow 600 may perform patient characteristics adjustments. For example, the variation of baseline of signal in time series may be associated with patient physical characteristics, such as skin color. Accordingly, adjustments may be performed to adjust the baseline based on patient characteristics, such as skin color, skin tone, race, and/or the like.

At block 628, logic flow 600 may determine a peak point. For example, a peak point may be detected which is related to the moving amplitude of blood volume. At block 630, logic flow 600 may perform a regression analysis. For example, line regression analysis may be performed to determine a relationship between blood flow and the peak point of CNP in time series signal. In some embodiments, moving average and peak detection may be used to identify the maximun displacement of the skin above the access site (for instance, AVF) from the time series signals.

Clinical Study: HD Patients With AFV Failures

Figure 7:
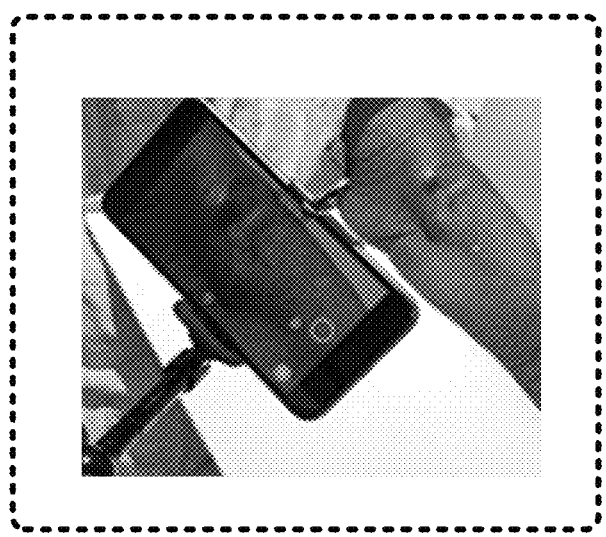
FIG. 7 depicts the capture of a video of a target area in accordance with the present disclosure.

A Clinical Study of HD patients was performed using an access site analysis process according to some embodiments. The HD patients were identified as having AVF failures (stenosis) and were targeted for an endovascular intervention involving the following steps: 1) pre-intervention assessment; 2) balloon angioplasty; 3) post-intervention assessment. The ABF was measured pre- and post-intervention by thermodilution using an HVT100 device. In addition, X-ray images were done to identify the location of the stenosis. Using a smartphone, videos were captured of AVF and the skin above the AVF with patients in a sitting position. FIG. 7 depicts the capture of a video of a target area according to some embodiments. The patients' race, gender, body mass, height, body mass index (BMI), and blood pressure were recorded.

The video-taped area had a length of about 10 cm and a width of about 5 cm. The distance between the smartphone and the AVF was approximately 25 cm. The video was recorded for 60 seconds with a 1080 p resolution and 30 frames per second (fps).

The video images were processed according to the steps of logic flow 600 of FIG. 6. For example, the video was preprocessing to make sure the video was quantified for the next steps of the analysis. Determination of the motion amplitude was made by converting CNP of pixels between two frames in the video sequence into a time series waveform. A band pass filter (0.02 Hz-2 kHz) was used to reduce unrelated signals. Every 10 seconds of time series data were transformed to frequency domain by fast Fourier transform (FFT). The average of the squared ratio of maximum-to-median power (M2) was then calculated (see, for example, FIG. 4) and used as an independent variable in a multiple regression model that related ABF (dependent variable) to the following independent variables: age, rice, and BMI of the patient.

Referring to FIG. 4, therein is depicted an example of frequency domain analysis using video information captured from a patient participating in the Clinical Study. As shown in graph 405, the maximum (MAX) spectral power 420 of $7.14 \times 10^3$ pixel (line 430) appears at a frequency of 2.2 Hz and the median (MED) spectral power 422 of $1.41 \times 10^3$ pixel is indicated at line 432. The square of ratio of MAX to MED (M2) is computed as $(7.14/1.41)^2 = 25.64$ and used as a predictor of the ABF rate.

Figure 8:
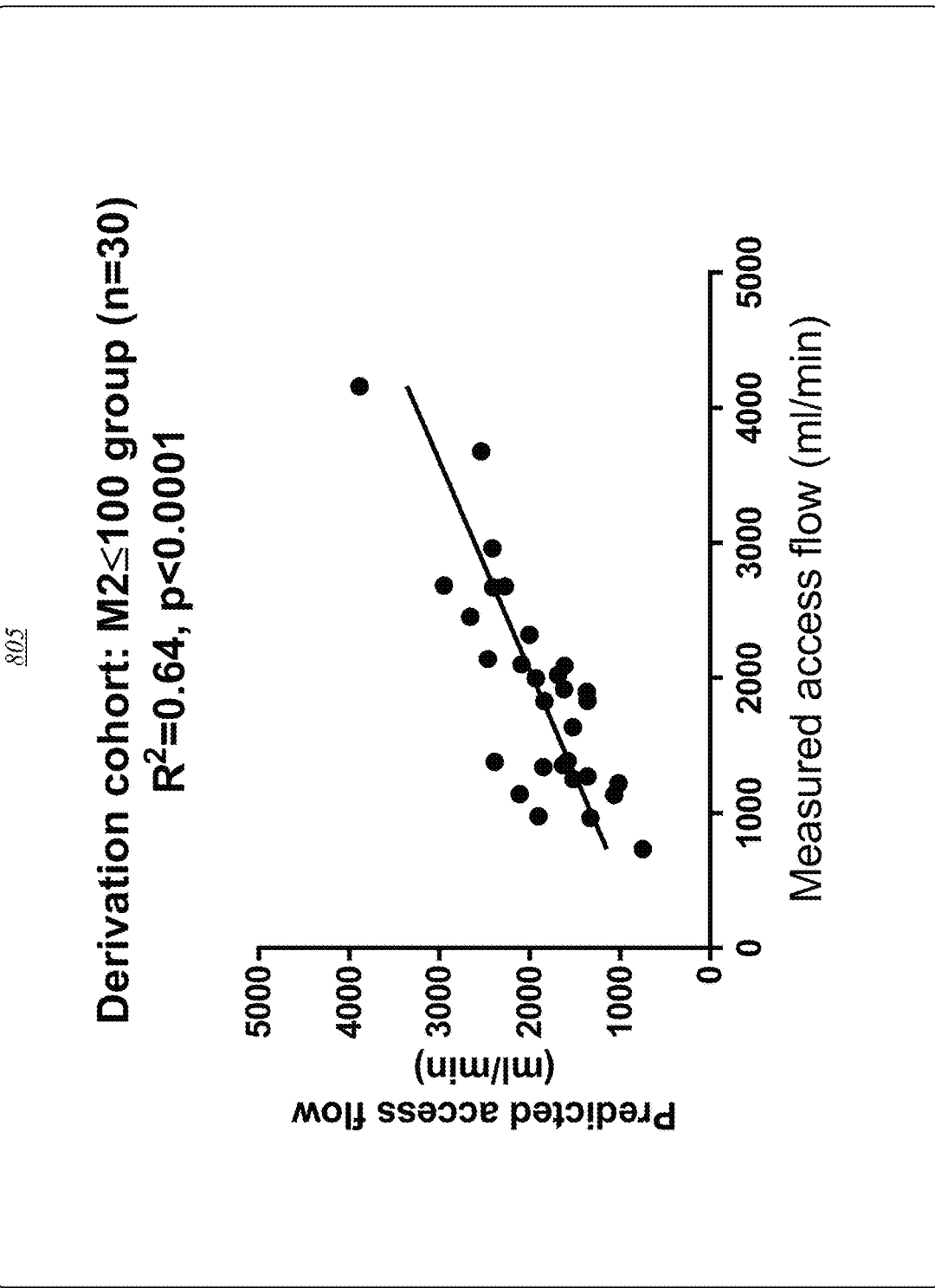
FIG. 8 illustrates a first graph of predicted access site flow rates versus measured access flow rates in accordance with the present disclosure.
Figure 9:
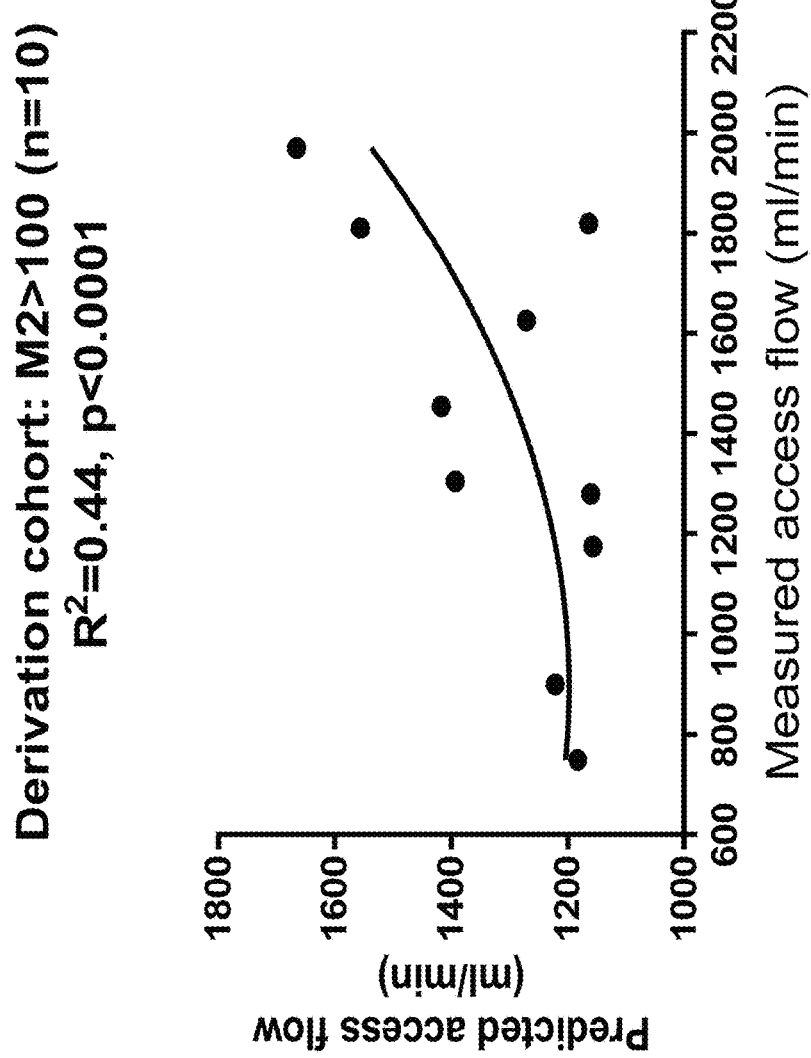
FIG. 9 illustrates a second graph of predicted access site flow rates versus measured access flow rates in accordance with the present disclosure.

FIGS. 8 and 9 show the correlations between measured and predicted ABF in patients from the derivation cohort with M2<=100 (graph 805 of FIGS. 8) and M2>100 (graph 905 of FIG. 9), respectively. In this clinical study, the ABF was measured by an HVT100 thermal dilution device (i.e., a "gold standard" of ABF measurement). Graph 905 depicts a curve fitting in the group with M2>100. Access flow was measured with the HVT100 device and predictions were made based on M2 calculations.

Figure 10:
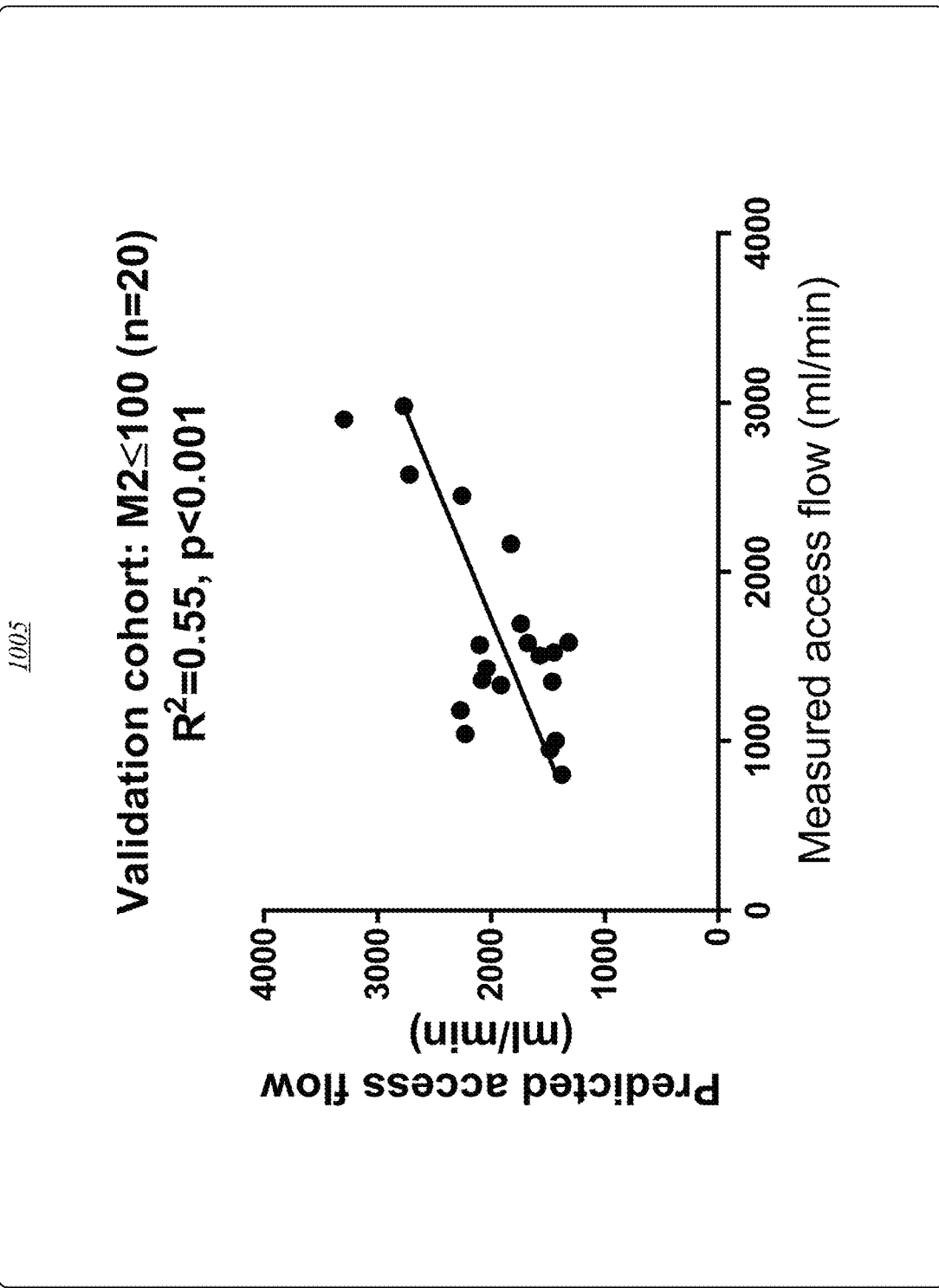
FIG. 10 illustrates a third graph of predicted access site flow rates versus measured access flow rates in accordance with the present disclosure.
Figure 11:
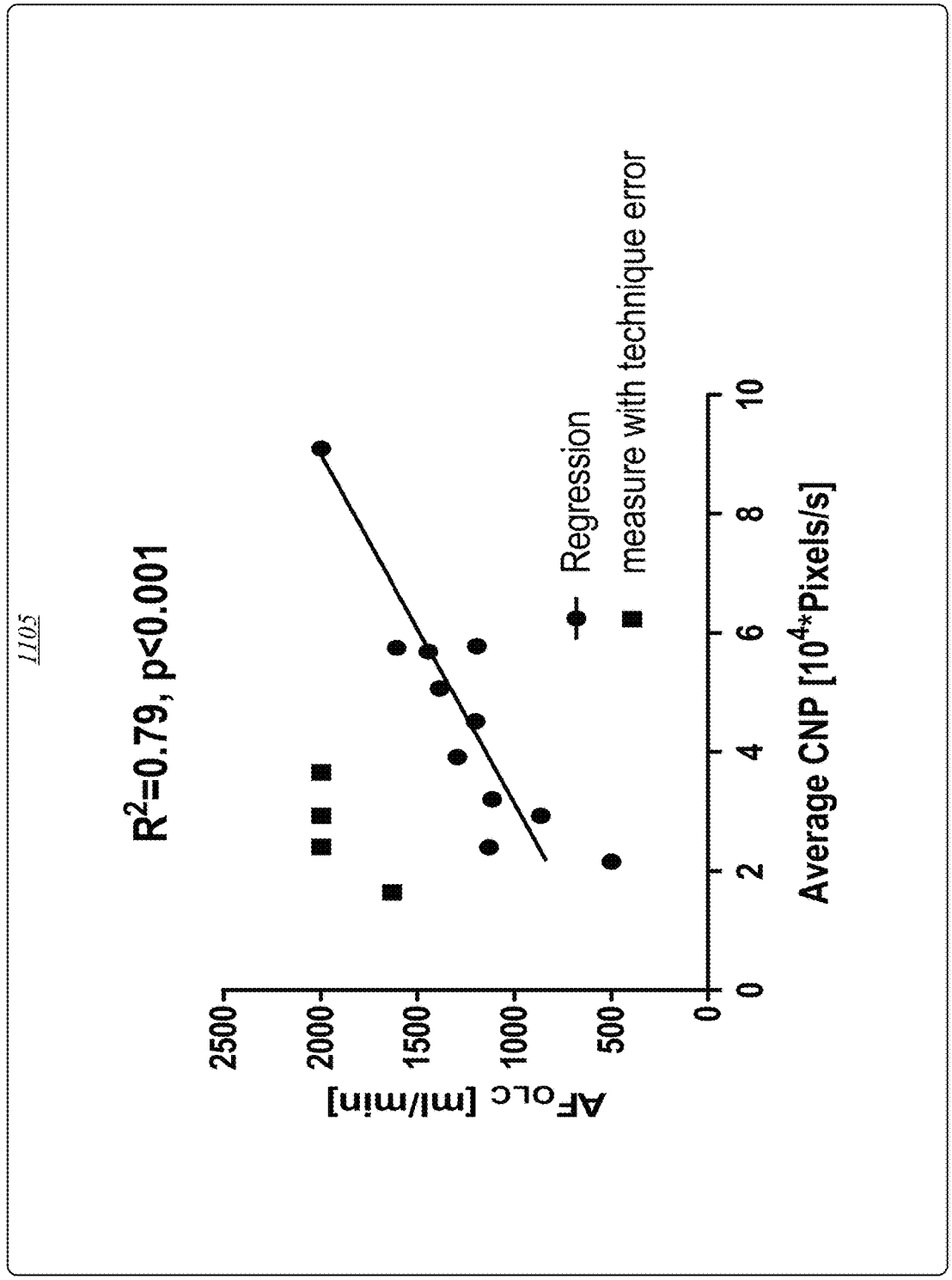
FIG. 11 illustrates a graph of measured access site flow rates versus the change in the number of pixels (CNP) in accordance with the present disclosure.

FIG. 10 depicts graph 1005 of the correlation between measured and predicted ABF in patients from a validation cohort. In particular, the multiple regression model developed in the derivation cohort was then evaluated in a validation cohort for patients with M2<=100. FIG. 11 depicts graph 1105 of the relationship between CNP in a time domain analysis and ABF determined by routine online conductivity measurement ($ABF_{OLC}$) in 15 patients.

Figure 12:
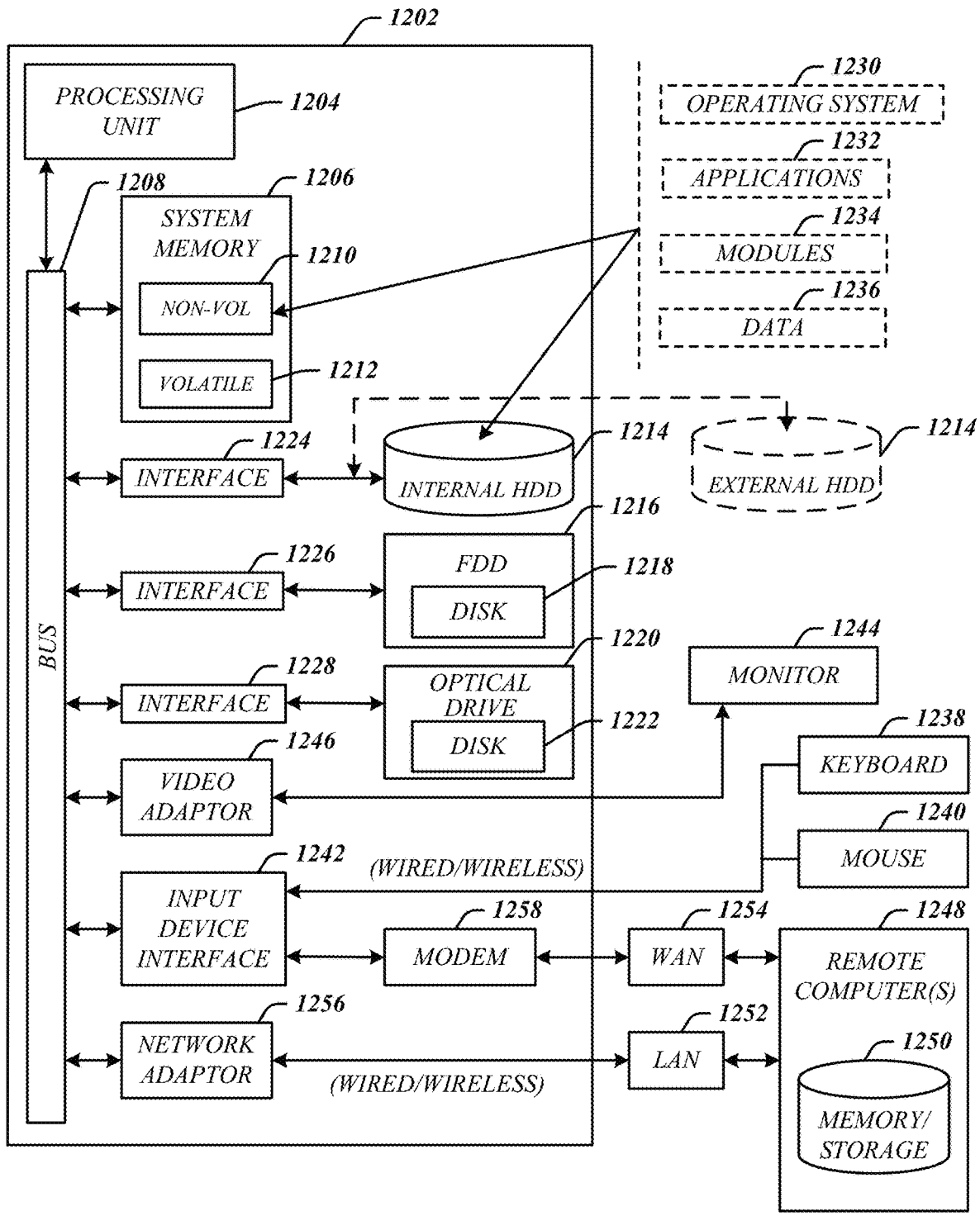
FIG. 12 illustrates an embodiment of a computing architecture in accordance with the present disclosure.

FIG. 12 illustrates an embodiment of an exemplary computing architecture 1200 suitable for implementing various embodiments as previously described. In various embodiments, the computing architecture 1200 may comprise or be implemented as part of an electronic device. In some embodiments, the computing architecture 1200 may be representative, for example, of computing device 110. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 1200. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1200 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1200.

As shown in FIG. 12, the computing architecture 1200 comprises a processing unit 1204, a system memory 1206 and a system bus 1208. The processing unit 1204 may be a commercially available processor and may include dual microprocessors, multi-core processors, and other multi-processor architectures.

The system bus 1208 provides an interface for system components including, but not limited to, the system memory 1206 to the processing unit 1204. The system bus 1208 can be any of several types of bus structure that may further interconnect to a memory bus (with or without a memory controller), a peripheral bus, and a local bus using any of a variety of commercially available bus architectures. Interface adapters may connect to the system bus 1208 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1206 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 12, the system memory 1206 can include non-volatile memory 1210 and/or volatile memory 1212. A basic input/output system (BIOS) can be stored in the non-volatile memory 1210.

The computer 1202 may include various types of computer-readable storage media in the form of one or more lower speed memory units, including an internal (or external) hard disk drive (HDD) 1214, a magnetic floppy disk drive (FDD) 1216 to read from or write to a removable magnetic disk 1211, and an optical disk drive 1220 to read from or write to a removable optical disk 1222 (e.g., a CD-ROM or DVD). The HDD 1214, FDD 1216 and optical disk drive 1220 can be connected to the system bus 1208 by a HDD interface 1224, an FDD interface 1226 and an optical drive interface 1228, respectively. The HDD interface 1224 for external drive implementations can include at least one or both of Universal Serial Bus (USB) and IEEE 1114 interface technologies.

The drives and associated computer-readable media provide volatile and/or nonvolatile storage of data, data structures, computer-executable instructions, and so forth. For example, a number of program modules can be stored in the drives and memory units 1210, 1212, including an operating system 1230, one or more application programs 1232, other program modules 1234, and program data 1236. In one embodiment, the one or more application programs 1232, other program modules 1234, and program data 1236 can include, for example, the various applications and/or components of computing device 110.

A user can enter commands and information into the computer 1202 through one or more wired/wireless input devices, for example, a keyboard 1238 and a pointing device, such as a mouse 1240. These and other input devices are often connected to the processing unit 1204 through an input device interface 1242 that is coupled to the system bus 1208, but can be connected by other interfaces.

A monitor 1244 or other type of display device is also connected to the system bus 1208 via an interface, such as a video adaptor 1246. The monitor 1244 may be internal or external to the computer 1202. In addition to the monitor 1244, a computer typically includes other peripheral output devices, such as speakers, printers, and so forth.

The computer 1202 may operate in a networked environment using logical connections via wired and/or wireless communications to one or more remote computers, such as a remote computer 1248. The remote computer 1248 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1250 is illustrated. The logical connections depicted include wired/wireless connectivity to a local area network (LAN) 1252 and/or larger networks, for example, a wide area network (WAN) 1254. Such LAN and WAN networking environments are commonplace in offices and companies, and facilitate enterprise-wide computer networks, such as intranets, all of which may connect to a global communications network, for example, the Internet.

The computer 1202 is operable to communicate with wired and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. An apparatus, comprising:
frequency domain filter circuitry;
at least one processor coupled to the frequency domain filter circuitry;
a memory coupled to the at least one processor, the memory comprising instructions that, when executed by the at least one processor, cause the at least one processor to:
generate video information based on a video of a dialysis access site of a patient,
determine change in the number of pixels (CNP) information of the video information, the CNP information associated with movement of a skin surface of the patient due to blood flow through the dialysis access site,
convert the CNP information to a CNP time series;
attenuate, via the frequency domain filter circuitry and the CNP time series, the CNP information;
determine frequency domain information of the attenuated CNP information,
determine a maximum-to-median power (M2) value of the frequency domain information, the M2 defined as $(MAX/MED)^2$, wherein MAX is a maximum waveform at a specific frequency in the frequency domain and MED is a median of all frequency ranges in the frequency domain, and
determine at least one access site characteristic based on the M2 value.

2. The apparatus of claim 1, the at least one access site characteristic comprising an access blood flow (ABF) rate.

3. The apparatus of claim 1, the at least one access site characteristic comprising an access site failure condition.

4. The apparatus of claim 1, the instructions, when executed by the at least one processor, to cause the at least one processor to perform a regression analysis of the M2 value based on at least one patient characteristic to determine the at least one access site characteristic.

5. The apparatus of claim 1, the instructions, when executed by the at least one processor, to cause the at least one processor to perform the regression analysis with access blood flow (ABF) rate as a dependent variable and the at least one patient characteristic as an independent variable.

6. The apparatus of claim 1, the instructions, when executed by the at least one processor, to cause the at least one processor to determine CNP as a change of a characteristic of pixels in an area of interest in the video.

7. The apparatus of claim 6, the characteristic comprising one of color or intensity.

8. The apparatus of claim 1, the instructions, when executed by the at least one processor, to cause the at least one processor to perform a time domain analysis of the video information via:
performing an amplitude analysis of the time series of CNP, and determining a peak point of the time series of CNP.

9. A method, comprising:
generating video information based on a video of a dialysis access site of a patient;
determining change in the number of pixels (CNP) information of the video information, the CNP information associated with movement of a skin surface of the patient due to blood flow through the dialysis access site;
converting the CNP information to a CNP time series;
attenuating, via the frequency domain filter circuitry and the CNP time series, the CNP information;
determining frequency domain information of the attenuated CNP information;
determining a maximum-to-median power (M2) value of the frequency domain information, the M2 defined as $(MAX/MED)^2$, wherein MAX is a maximum waveform at a specific frequency in the frequency domain and MED is a median of all frequency ranges in the frequency domain; and
determining at least one access site characteristic based on the M2 value.

10. The method of claim 9, the at least one access site characteristic comprising an access blood flow (ABF) rate.

11. The method of claim 9, the at least one access site characteristic comprising an access site failure condition.

12. The method of claim 9, comprising performing a regression analysis of the M2 value based on at least one patient characteristic to determine the at least one access site characteristic.

13. The method of claim 9, comprising performing the regression analysis with access blood flow (ABF) rate as a dependent variable and the at least one patient characteristic as an independent variable.

14. The method of claim 9, comprising determining CNP as a change of a characteristic of pixels in an area of interest in the video.

15. The method of claim 14, the characteristic comprising one of color or intensity.

16. The method of claim 9, comprising performing a time domain analysis of the video information via:
performing an amplitude analysis of the time series of CNP, and determining a peak point of the time series of CNP.

* * * * *